(12) United States Patent
Hösel et al.

(10) Patent No.: US 7,143,479 B2
(45) Date of Patent: Dec. 5, 2006

(54) INSPECTION DEVICE ON A SPINNING PREPARATION MACHINE, ESPECIALLY A CARDING MACHINE, CLEANER OR THE LIKE

(75) Inventors: Fritz Hösel, Mönchengladbach (DE); Armin Leder, Mönchengladbach (DE)

(73) Assignee: Trutzschler GmbH & Co. KG, Monchengladbach (DE)

( * ) Notice: Subject to any disclaimer, the term of this patent is extended or adjusted under 35 U.S.C. 154(b) by 10 days.

(21) Appl. No.: 10/737,916

(22) Filed: Dec. 18, 2003

(65) Prior Publication Data

US 2004/0128799 A1 Jul. 8, 2004

(30) Foreign Application Priority Data

Dec. 19, 2002 (DE) ................. 102 59 475

(51) Int. Cl.
*D01G 15/00* (2006.01)
(52) U.S. Cl. ........................................... 19/98
(58) Field of Classification Search ............... 19/98, 19/105, 106 R, 200, 203, 204, 205; 700/130, 700/139, 142, 143, 144; 57/264, 265
See application file for complete search history.

(56) References Cited

U.S. PATENT DOCUMENTS

| | | | |
|---|---|---|---|
| 4,805,266 A * | 2/1989 | Leifeld et al. ................. | 19/0.2 |
| 4,813,104 A | 3/1989 | Hollingsworth et al. | |
| 4,858,277 A * | 8/1989 | Pinto et al. .................... | 19/200 |
| 5,125,514 A * | 6/1992 | Oehler et al. ................. | 209/590 |
| 5,130,559 A * | 7/1992 | Leifeld et al. .......... | 250/559.11 |
| 5,131,515 A | 7/1992 | Scamardo | |
| 5,642,553 A * | 7/1997 | Leifeld ........................... | 19/98 |
| 5,692,622 A * | 12/1997 | Hergeth ........................ | 209/580 |
| 5,761,771 A * | 6/1998 | Leifeld ........................... | 19/200 |
| 5,819,373 A * | 10/1998 | Schlichter et al. ............. | 19/205 |
| 5,917,591 A | 6/1999 | Schlichter | |
| 5,930,869 A * | 8/1999 | Faas et al. ...................... | 19/98 |
| 6,029,317 A * | 2/2000 | Meile et al. ................ | 19/145.5 |
| 6,298,522 B1* | 10/2001 | Rubenach ..................... | 19/204 |
| 6,477,741 B1* | 11/2002 | Hosel ............................ | 19/107 |
| 6,647,595 B1* | 11/2003 | Schurenkramer et al. . | 19/106 R |
| 2001/0006220 A1* | 7/2001 | Fritz ...................... | 250/559.46 |

FOREIGN PATENT DOCUMENTS

| | | |
|---|---|---|
| DE | 37 34 145 A1 | 4/1989 |
| DE | 39 12 737 C2 | 10/1990 |
| DE | 39 28 279 C2 | 2/1991 |
| DE | 195 14 039 A1 | 10/1996 |
| DE | 100 55 026 A1 | 5/2002 |
| EP | 0 606 626 A1 | 7/1994 |

* cited by examiner

Primary Examiner—Gary L. Welch
(74) Attorney, Agent, or Firm—Venable LLP; Robert Kinberg; Steven J. Schwarz (57) ABSTRACT

In a device on a spinning preparation machine, especially a carding machine, cleaner or the like, having a machinery housing, the machine and/or fiber feed and fiber discharge devices are arranged in the interior of the machinery housing.

In order that the fiber material located inside a housing can be inspected and checked in a simple manner from outside the housing, without the housing being removed, in the interior of the machinery housing there is at least one electronic camera (video camera) which is associated with the textile fiber material and/or a machine element for displaying an image of the surface of the textile fiber material and/or the machine element.

25 Claims, 7 Drawing Sheets

INSPECTION DEVICE ON A SPINNING PREPARATION MACHINE, ESPECIALLY A CARDING MACHINE, CLEANER OR THE LIKE

CROSS REFERENCE TO RELATED APPLICATION

This application claims the priority of German Patent Application No. 102 59 475.9, which is incorporated herein by reference.

BACKGROUND OF THE INVENTION

The invention relates to a device on a spinning preparation machine, especially a carding machine, cleaner or the like, having a machinery housing, in which the machine and/or fiber feed and fiber discharge devices are arranged in the interior of the machinery housing.

In practice, carding machines are encased in a machinery housing of sheet metal or other materials. The casing serves for the safeguarding of the machine, for protection against spinning-mill dust, for the visual appearance and for protection against accidents. The machines are also enclosed in a housing in order to cover operating units on technological or airflow-related grounds. As a result, the user is generally often unable to carry out a visual inspection of certain production and quality-determining operations.

In a known device on a carding machine having a machinery housing (U.S. Pat. No. 4,813,104), a housing frame carries wall elements, so that a closed housing is formed. The housing comprises lateral wall elements, front wall elements, rearward wall elements and a top element. The housing frame comprises four horizontal base supports, four horizontal upper supports and four vertical supports, which may also consist of steel tubing. The known machinery housing consists of supports and struts, doors and flaps. In order to be able to inspect the fiber material inside the machine, doors and flaps have to be opened or dismantled. Dismantling is associated with screwing/unscrewing work which is often very considerable. The supports and struts cannot be dismantled for static reasons, but they limit the scope for inspection very substantially. A particular disadvantage is that the fiber material cannot be inspected from a remote location outside the machinery housing, either close to the machine or further away from the machine. In addition, machine elements such as fiber-guiding, rotating rollers inside the machinery housing in some cases have cover elements, e.g. cover panels, which are themselves non-transparent.

The problem underlying the invention is therefore to provide a device of the kind described at the beginning which avoids the mentioned disadvantages and which especially enables the fiber material located inside a housing and/or machine elements arranged therein to be inspected and checked from outside the housing in a simple manner, without the housing being removed.

SUMMARY OF THE INVENTION

The invention provides a spinning preparation machine comprising a housing having a housing interior and at least one working element housed at least partly within said housing interior, wherein the machine further comprises at lease one image-recording system which is arranged to generate an image of a surface of a said working element or of textile fiber material within said housing interior.

The invention additionally provides a device on a spinning preparation machine, especially a carding machine, cleaner or the like, having a machinery housing, in which the machine and/or fiber feed and fiber discharge devices are arranged in the interior of the machinery housing, wherein the interior of the machinery housing there is at least one electronic image-recording system (for example, video camera) which is associated with the textile fiber material and/or a machine element for displaying an image of the surface of the textile fiber material and/or the machine element.

As a result of the features of the invention it is possible, by displaying images on the monitor of a machine operation terminal or a higher order central system operation terminal, for all important operations to be assessed and viewed immediately from one location. Cameras having lighting devices may be mounted at the necessary and strategically important points of, for example, a carding machine in such a manner that they provide images of the desired locations. The cameras are connected to evaluation units, which are located, for example, in the machine controller. The evaluation units provide, for example by means of a central unit of the control system, corresponding images to the machine operation and display station. The latter is so configured that it is capable of displaying such images, that is to say it has a monitor. An inspector can, as necessary, select between a plurality of cameras showing images of different locations. It is also possible to display a plurality of images simultaneously. A particular advantage is that the fiber material which is located in the interior of the housing and which is not or is only barely discernible from the outside can be inspected reliably and clearly. A further special advantage is that it is possible to make use of the electronic machine and/or system controller present in modern machines, only equipped with an evaluation unit and a monitor but otherwise entirely without additional expenditure.

According to DE-A-37 34 145, a device for cleaning and opening fiber material in flock form has, for ascertaining the degree of contamination of the fiber material, a linear diode array camera or television camera which is arranged outside a housing.

The arrangement may be such that the electrical signals from the electronic camera (video camera) are transmittable to outside the machinery housing. The signals may be processible by an electronic image-processing device. The display device, e.g. monitor, may be arranged outside the machinery housing. The machinery housing may be of case-like structure. The machinery housing may be at least partly closed. The machinery housing may be completely closed. The electronic camera (video camera) may be connected to an image-processing device. The image processing device may be connected to a display device. The display device may be a monitor, e.g. a flat-screen monitor. The video signals may be processed electronically. The video signals or video images may be stored. The electronic camera (video camera) may be associated with a lighting device. The video camera may be associated with a flock filling chute associated with the machine. The electronic camera (video camera) may be associated with the flying fiber flocks in the filling chute. The electronic camera (video camera) may be associated with the fiber material feed to be fed into the machine. The electronic camera (video camera) may be associated with the fiber feed region of the machine. The electronic camera (video camera) may be associated with the fiber material located on a roller, e.g. clothed roller, needle roller. The electronic camera (video camera) may be associated with a licker-in of a carding machine. The electronic camera (video camera) may be associated with the cylinder of a carding machine. The electronic camera (video camera) may be associated with the fiber take-off region of the machine. The electronic camera (video camera) may be associated with the doffer of a carding machine. The electronic camera (video camera) may be associated with the stripper roller of a carding machine. The electronic camera (video camera) may be associated with the fiber material detached by the stripper roller of a carding machine. The electronic camera (video camera) may be associated with the fiber material located on at least one returning card top bar of a carding machine. The electronic camera (video camera) may be in fixed position. At least one extraction hood for extracting separated waste may be associated with an electronic camera (video camera). At least one electronic camera (video camera) may be integrated into the extraction lines through which separated waste is extracted. More than one electronic evaluation device may be present. More than one electronic camera (video camera) may be connected to at least one evaluation device. The at least one evaluation device may be connected to the associated machine controller. The images of the fiber material may be displayed on the machine operation and display unit. The images may be forwarded to other systems, e.g. higher order and central systems. Each machine may be associated with at least two electronic cameras (video cameras). At least two electronic cameras (video cameras) may be associated with a machine controller. The at least two electronic cameras (video cameras) may be connected to a central evaluation device. Different light sources may be provided. Light sources of different colours may be provided. At least one incident light source may be provided. The at least one electronic evaluation device (image-processing unit) may be connected to an electronic control and regulation device, for example a microcomputer. The electronic camera (video camera) may be associated with a central waste collection line. There may be a window for the camera in each waste collection line. There may be a window for a lighting device in each waste collection line.

The evaluated video images may be used for determining the ratio of good fiber content to the trash content. The evaluated video images may be used for assessing the quality of the fiber material being processed. A machine may be connected to a central evaluation device, to which more than one camera is connected. Digital image-processing may be used for the evaluation device. The electronic control and regulation device, for example a computer, may have a memory for video images. The image values of the electronic camera video camera may be convertible into electrical signals. On a spinning-mill machine, such as a carding machine, card, cleaner or the like, there may be at least two or more electronic cameras (video cameras) arranged one next to the other for detecting and assessing textile fiber material over the width of the textile machine. Measured values may be converted into electronic signals, the system being connected to an image-evaluation device (having a computer) which evaluates the raw data from the camera.

The textile fiber material may be selected from fiber sliver, fiber web and fiber flocks. The textile fiber material may be a card web or a fiber flock web. The textile material may be fiber waste. The fiber web at the outlet of a carding machine or card may be monitored. The web speed may be at least 40 m/min.

The sliver may be located on a high-speed roller, for example having clothing, needles, pins or the like. The high-speed roller may be arranged in an opener, cleaner, a carding machine, a card or the like. The quality of the sliver, especially of the fiber web, may be assessed. Foreign bodies, e.g. trash, metal or the like, holes, or irregularities in the sliver may be inspected. The monitoring regions of adjacent electronic cameras (video cameras) may have a certain degree of overlap. Each electronic camera (video camera) may have substantially one lens or the like and/or an image-recognition chip (sensor). The electronic camera (video camera) may be associated with at least one lighting unit. The monitoring regions may be adjacent to one another, without gaps, over the width. The total width region of the sliver, especially of the fiber web, may be monitored simultaneously. The cameras may be connected to a central evaluation device. The electronic cameras (video cameras) may be connected to a central evaluation device for the processing of image information. Evaluation devices may be provided between a central camera signal evaluation means and the individual or grouped electronic cameras (video cameras). The image evaluation device may cooperate with an electronic control and regulation device, for example a microcomputer. The sliver may be moved continuously. More than one electronic camera (video camera) may be arranged in columns and one next to the other. The electronic cameras (video cameras) may be arranged staggered relative to one another, seen in the direction of movement of the sliver. Monitoring or checking of the sliver located inside the textile machine, e.g. carding machine, card, cleaner or the like, may be provided. Monitoring or checking of a sliver entering and/or leaving a textile machine may be provided. The fiber orientation in an incoming and/or outgoing silver, especially a fiber web, may be inspected. The uniformity (homogeneity, distribution between fibers and cavities) of the sliver, especially the fiber web, may be inspected. Holes in the fiber web can be inspected. The web shape in the edge regions may be inspected. The fiber material located on the cylinder of a carding machine may be inspected.

In the case of a cleaning machine, checking of the degree of contamination of the incoming and/or outgoing fiber material can be provided. Assessment of the waste of the textile machine may be provided. The waste stream may be guided past, for example transported past, the electronic camera (video camera). Electronic cameras (video cameras) may be mounted at the waste removal devices, for example extraction hoods, for continuous monitoring of the waste. The system may comprise a plurality of blowing room machines. The system may comprise a plurality of carding machines. The video images may be effected on-line. The uniformity of the sliver, for example the fiber web, may be determinable by means of the lightness of the image. There may be a transparent window or the like between the electronic camera (video camera), especially the lens and the fiber material. There may be a device for keeping the lens and/or the window clean, for example free of dust, fiber fly or the like. The keeping-clean device may be pneumatic, for example in the form of a suction or blowing device. The fiber material may be monitored automatically and the machine or system is controlled or regulated in accordance with the evaluated images. A still image may be produced on the monitor. The electronic camera (video camera) may be in a fixed position. The electronic camera (video camera) may be movable over the width of the machine. The distance between the electronic camera (video camera) and the textile fiber material may be adjustable. The machine element may be the clothing of a roller. The electronic camera (video camera) may have a lens. The electronic camera (video camera) may have a CCD sensor. The electronic camera (video camera) may have a signal conversion device. The electronic camera (video camera) may have a power supply device.

DESCRIPTION OF THE PREFERRED EMBODIMENTS

Figure 1A:
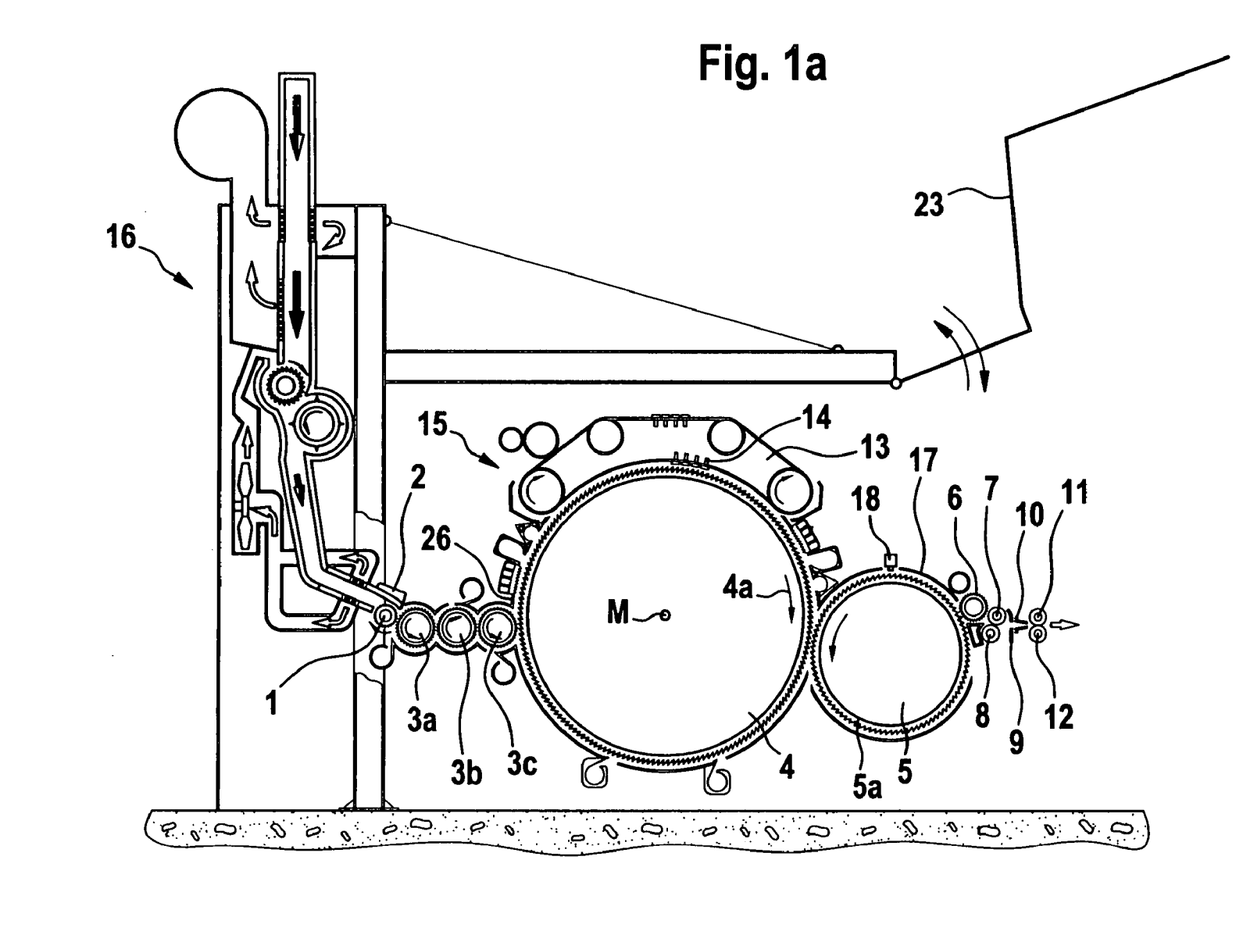
FIG. 1a is a diagrammatic side view of a carding machine having the device according to the invention with the machinery housing opened.

FIG. 1a shows a carding machine 15, for example a high performance carding machine of the kind made by Trützschler GmbH & Co. KG of Mönchengladbach, Germany and known as the DK 903, having a feed roller 1, feed table 2, lickers-in 3a, 3b, 3c, cylinder 4, doffer 5, stripper roller 6, nip rollers 7, 8, web guide element 9, sliver funnel 10, delivery rollers 11, 12 and revolving card top 13 with card top bars 14. The directions of rotation of the rollers are indicated by curved arrows. Reference letter A denotes the operating direction. Upstream of the carding machine 15 there is located a flock feeder 16, e.g. of the kinds made by the above-mentioned Trutzschler GmbH and Co, KG and known as the Direktfeed DFK. The machinery housing for the carding machine 15 has as housing elements doors and flaps, which are mounted on support elements, and are able to uncover and close openings in the machinery housing (see FIG. 1b). In the upper cover 17 of the doffer 5 there is an opening which is associated with a video camera 18 capable of producing an image of the clothing 5a of the doffer 5 with or without fiber material.

Figure 1B:
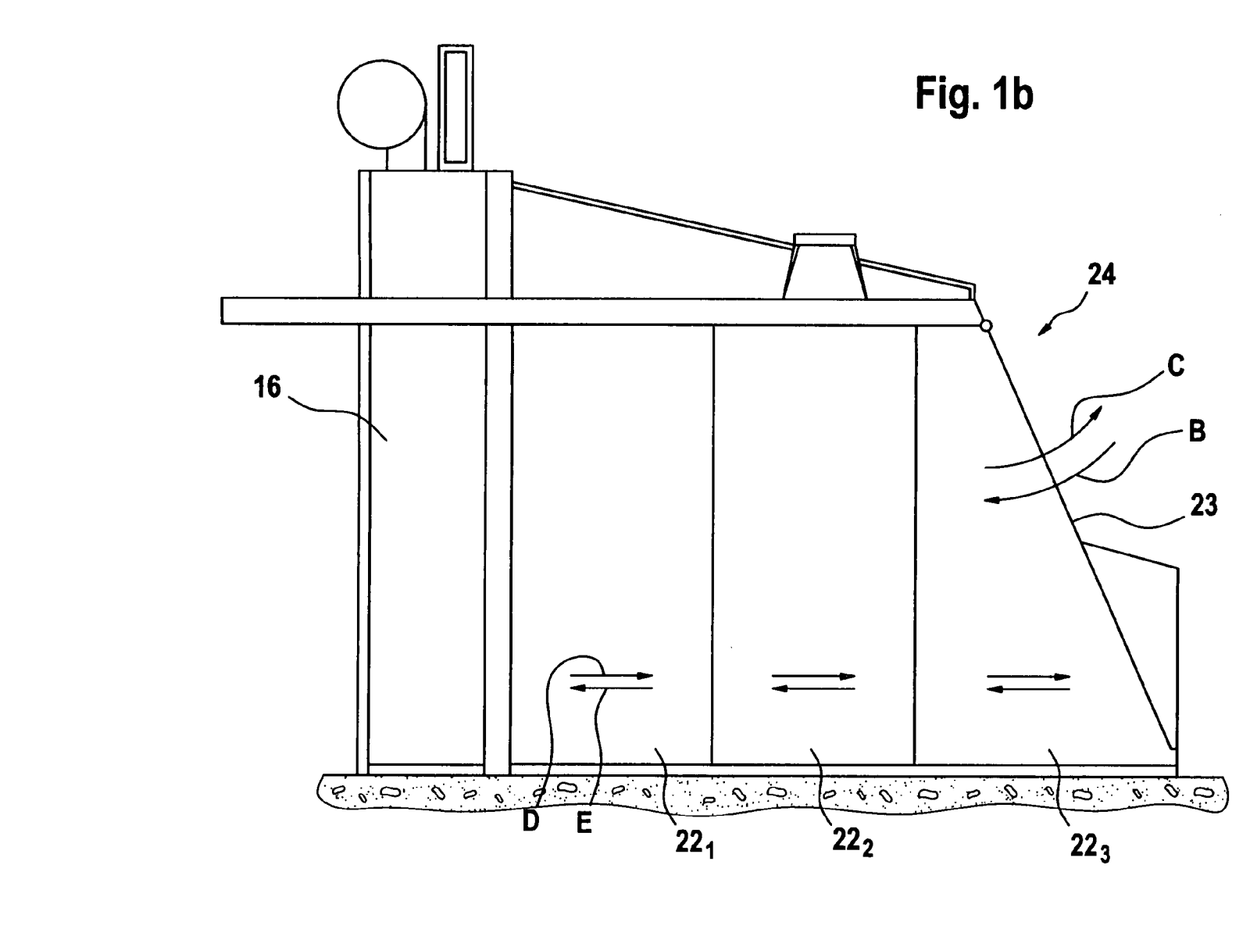
FIG. 1b is a side view of the machinery housing according to FIG. 1a closed.

According to FIG. 1b, the carding machine 15 (see FIG. 1a) is arranged in the interior of the machinery housing 24. The machinery housing 24 has three doors $22_1$, $22_2$, $22_3$ in one side region. In its other side region (not shown) the carding machine 15 has three further doors $22_4$, $22_5$, $22_6$.

The doors of $22_1$ to $22_6$ are displaceable in the direction of arrows D, E. At the front end, or output end, of the carding machine 15, the machinery housing 24 has a pivotable cover flap 23. Furthermore, a cover plate (not shown) is provided above the carding machine 15. At the rear end, or input end, of the carding machine 15, the chamber in which the carding machine 15 is located below the machinery housing 24 is bounded or covered by the flock feeder device 16. The doors $22_1$ to $22_3$ (and the doors $22_4$ to $22_6$ correspondingly) are displaced along rails in the direction of arrows D, E until the side region of the carding machine 15 has been uncovered or closed, as the case may be. The video cameras (18 in FIG. 1a; $18_1$ to $18_4$ in FIG. 7) in the interior of the machinery housing 24 produce an image of the surface of fiber material and/or machine elements below the machinery housing 24 and transmit the electronic image signals to the machine controllers and display devices arranged outside the machinery-housing 24; 24a, 24b.

Figure 2:
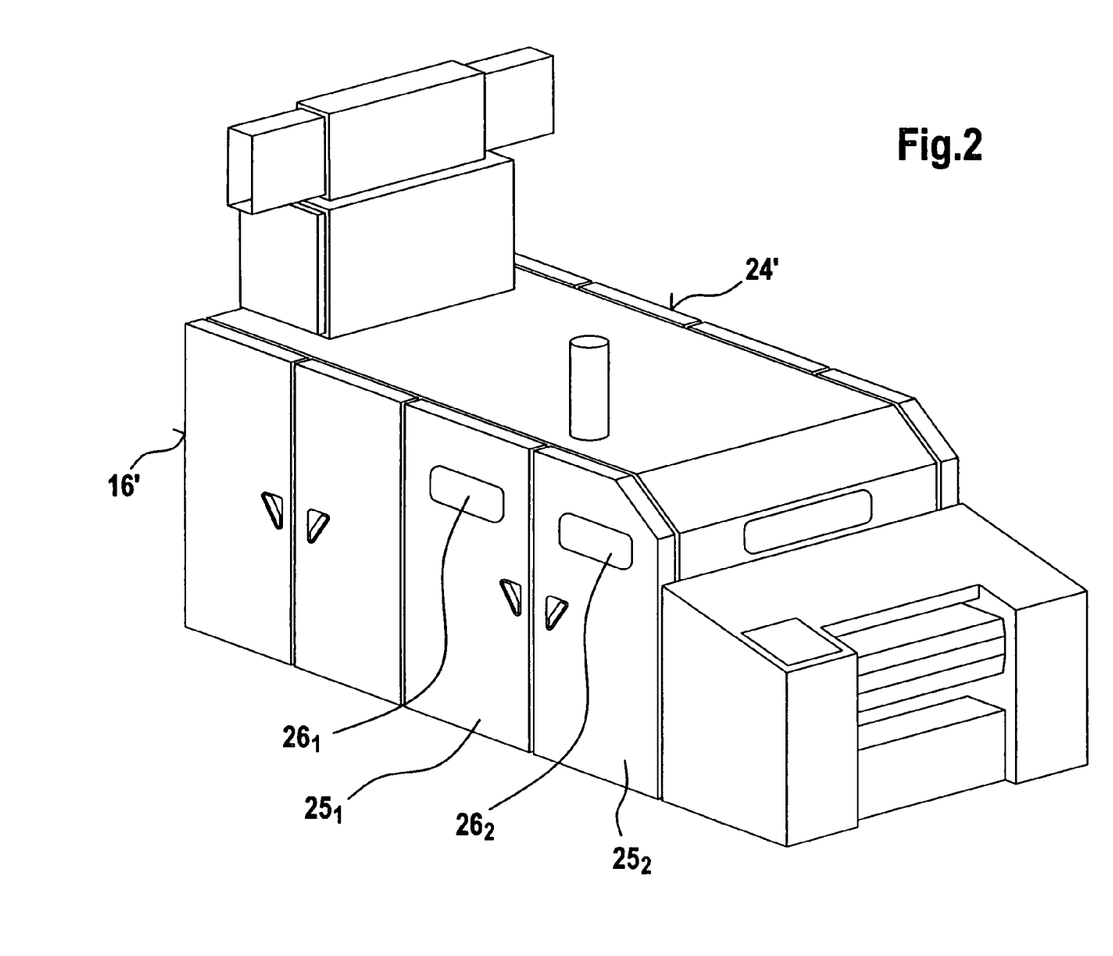
FIG. 2 is a perspective view of a further variant of a closed machinery housing for a carding machine having a flock feeder device.

Inside the closed machinery housing 24' of a further variant in accordance with FIG. 2 there are arranged the carding machine 15 (not shown) and the video cameras 18 (not shown). In the side doors $25_1$, $25_2$ there are windows $26_1$, $26_2$ which, although allowing some view of the interior of the machinery housing 24', do not allow detailed and, above all, close inspection (small distance) of the machine elements with or without fiber material. Reference numeral 16' denotes the machinery housing around the flock feeder device 16.

Figure 3:
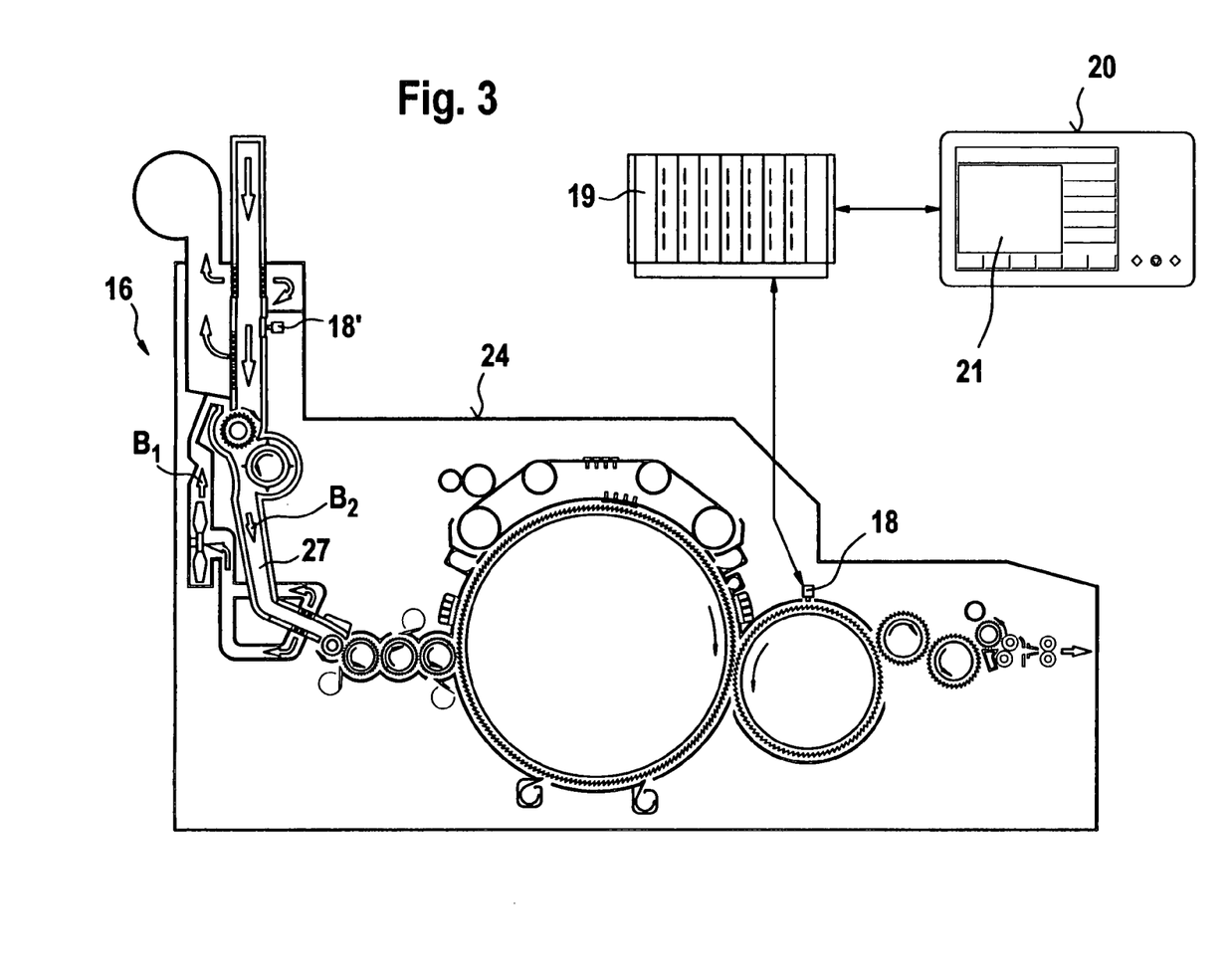
FIG. 3 shows the association of a video camera with the doffer of a carding machine and a block diagram with a machine control device and a machine operation and display device having a monitor.

According to FIG. 3, the video camera 18 is electrically connected to the carding machine controller 19, for example of the kind known as the TMS-2 made by the above mentioned Trützschler GmbH and Co. KG, to which the carding machine operation and display device 21 is connected. The operation and display device has a monitor 21 which enables the images from the video camera 18 to be displayed. In this way, the carding machine 15, or parts thereof, located in the interior of the machinery housing 24 can be inspected from outside the machinery housing 24. It is important that in the case of existing closed machinery housings, for example on carding machines or draw frames, it is nevertheless possible with the aid of the installed cameras 18 for information from the interior to be transmitted to the outside, namely to the existing machine operation and display unit 20. That unit and the machine controller 19 are so configured that the image information generated by electronic video cameras 18 can be evaluated, forwarded and displayed. That also means that a suitable operation and display unit 20 has a correspondingly suitable monitor 21 or a corresponding display. It is accordingly possible for the operating or servicing personnel to identify and assess important machine states without the need to open or even dismantle the housing 24. A particular advantage of the device according to the invention is the fact that many of the images in question are obtainable when the machine 15 is running and in production. This thus avoids the situation where, in order to obtain equivalent information, the machine generally has to be stopped because only then can the doors of the housing 24 be opened. In some cases it is even necessary additionally to dismantle certain covers.

In accordance with FIG. 3, there is a window in a chute wall of the upper reserve chute of the flock feeder device 16, for example of the kind known as the EXACTAFEED FBK made by Trützschler GmbH and Co. KG, which window is associated with a video camera 18'. In this way the flying fiber flock material being conveyed pneumatically in the interior of the reserve chute can be inspected through the window by means of the video camera 18'. The video camera 18' is connected, for example, to the machine controller 19.

Figure 4:
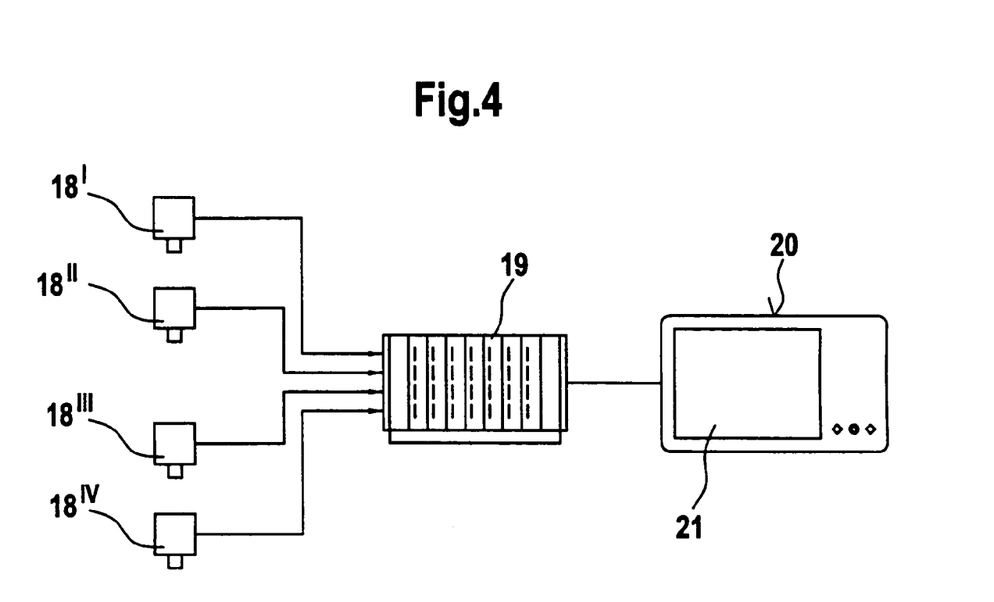
FIG. 4 shows a plurality of video cameras connected to an electronic control device and to an operation and display device having a monitor.
Figure 7:
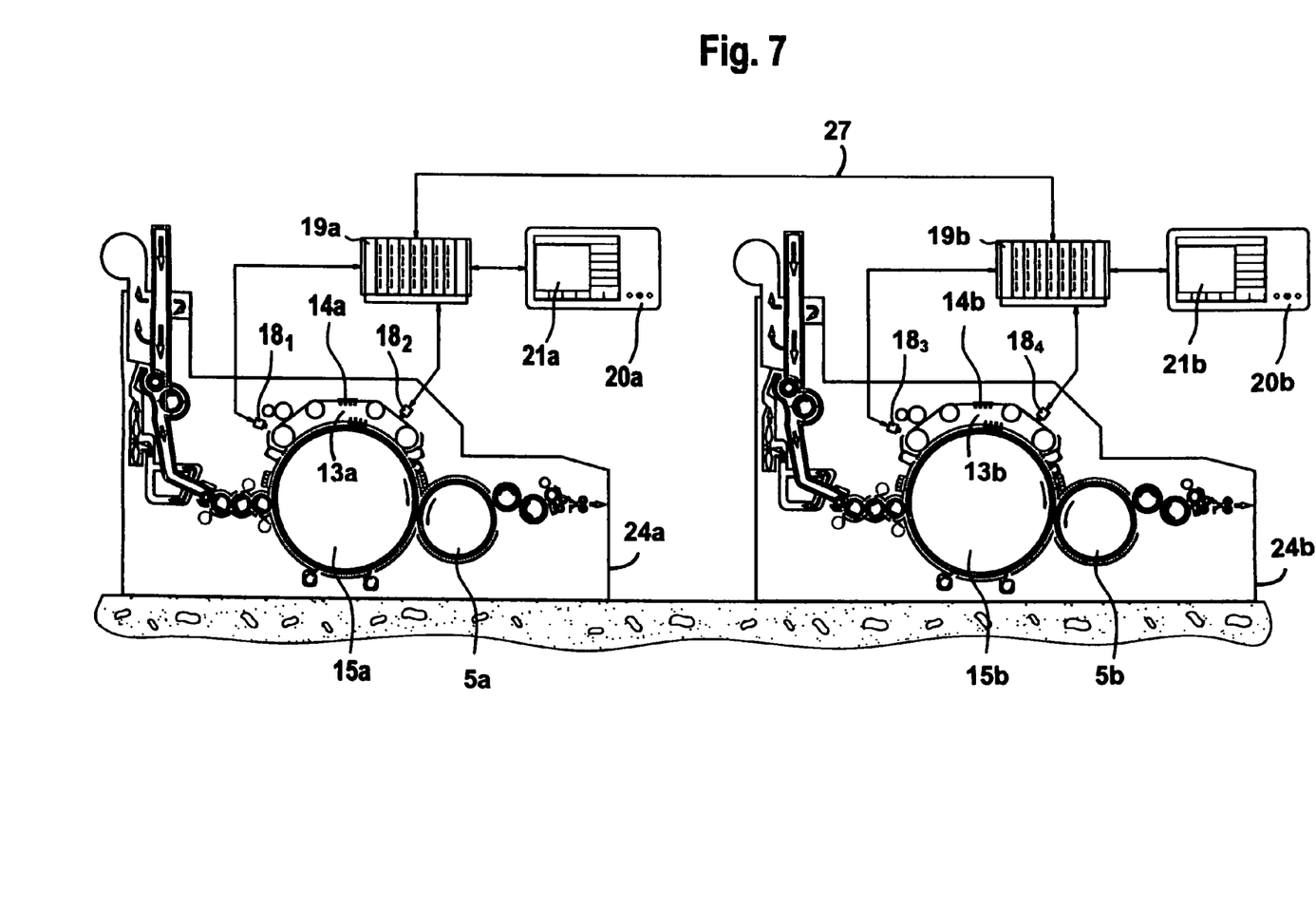
FIG. 7 shows the association of two video cameras with the revolving card tops of two carding machines, the respective connections to the associated machine controller and the associated operation and display unit, and also the electronic connection of the two machine control devices.

In accordance with FIG. 4, four video cameras $18^I$ to $18^{IV}$ are provided which may be present in the interior of the machinery housing 24 of a machine, for example carding machine 15, or in the interior of the machinery housing 24a to 24d of four different machines 15a to 15d (see in this connection FIG. 7). The video cameras $18^I$ to $18^{IV}$ are connected to a common electronic control and regulation device 19 to which an operation and display device 20 having at least one monitor 21 is connected. Where the video cameras $18^I$ to $18^{IV}$ are associated with different machines of a system, the control and regulation device 19 is a higher order system controller having a higher order display device 20.

Figure 5:
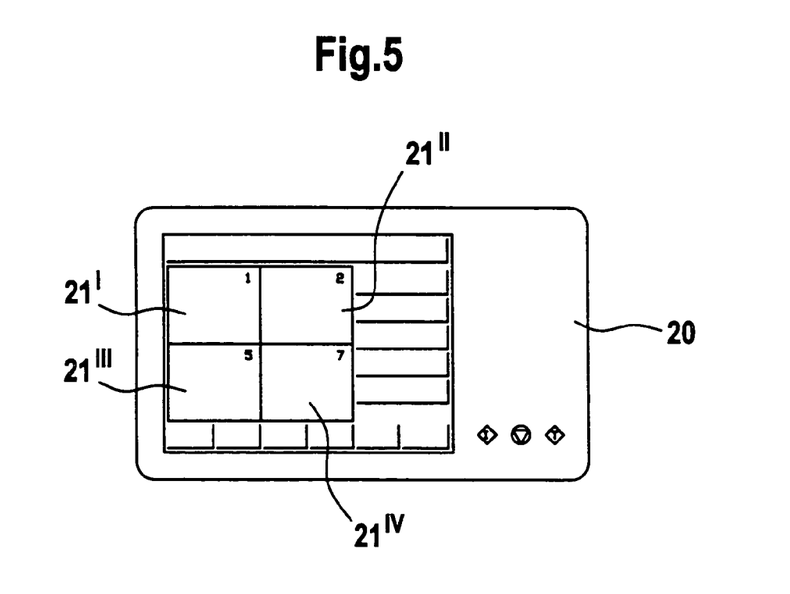
FIG. 5 illustrates the fiber material loading on the card top bars of a plurality of carding machines on an operation and display unit having four monitors.

According to FIG. 5, the display device 20 has four monitors $21^I$ to $21^{IV}$. In this way it is possible to display and inspect the card top loading, for example, of a plurality of machines (see FIG. 7) on one operation and display unit 20.

Figure 6:
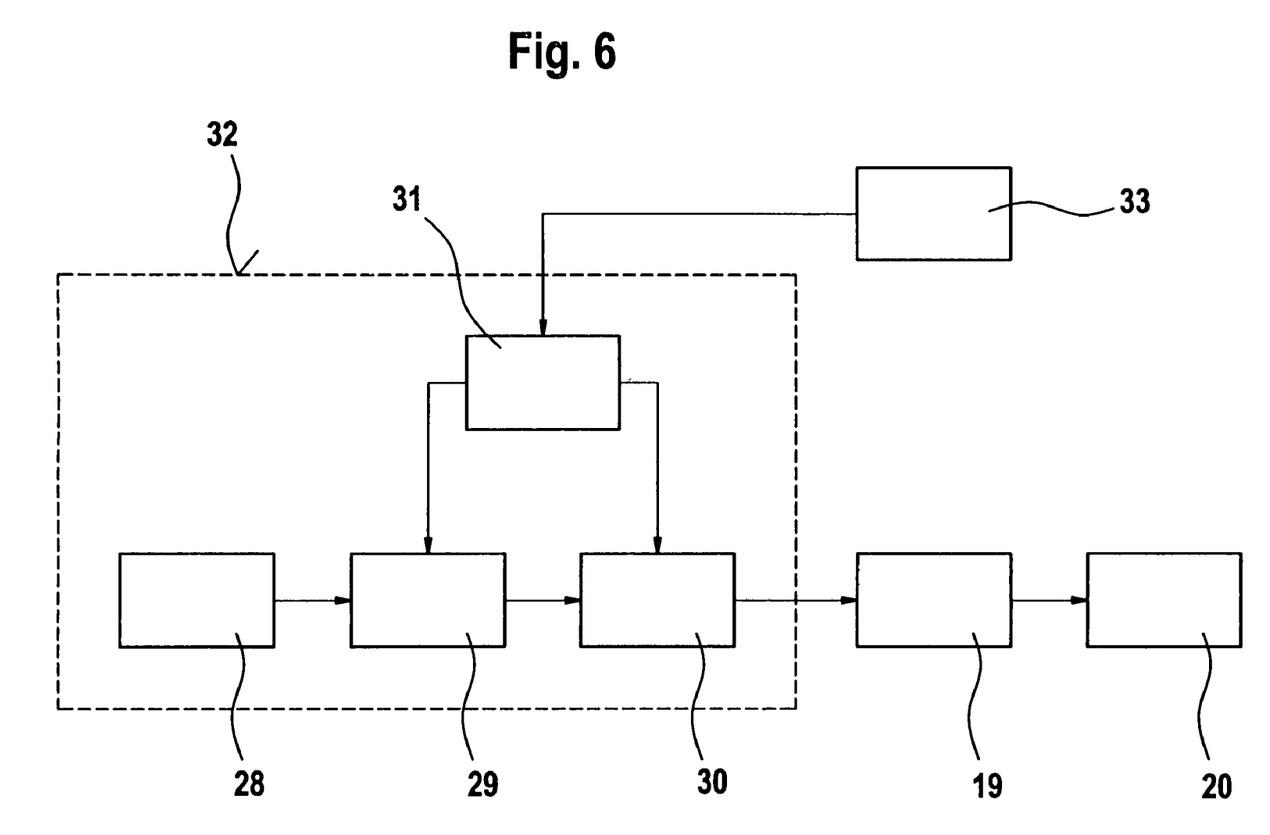
FIG. 6 is a diagrammatic side view of a video camera.

In the case of the video camera 18 (electronic camera) according to FIG. 6, the light rays reflected by an object are focussed by the camera lens 28 and projected by the latter onto a CCD sensor 29. The electronic signals obtained therein are converted in a signal conversion device 30 and made available for further processing. A power supply unit 31 supplies all the electronic components with the necessary currents. Reference numeral 32 denotes the camera housing and reference numeral 33 denotes an electronic power source.

FIG. 7 shows two carding machines 15a, 15b which are located in the interior of respective machinery housings 24a and 24b. The returning card top bars 14a, 14b of the revolving card tops 13a, 13b are each associated with two video cameras $18_1$, $18_2$ and $18_3$, $18_4$, with which the card top loading, that is to say the fiber material on the clothings of the card top bars 14a, 14b, is displayed. The video cameras $18_1$, $18_2$ are connected to the carding machine controller 19a of the carding machine 15a and the video cameras $18_3$, $18_4$ are connected to the carding machine controller 19b of the carding machine 15b. The carding machine controllers 19a, 19b are connected to respective operation and display devices 20a, 20b. The carding machine controllers 19a and 19b are electronically connected to one another by a communications network 27, e.g. of the kind supplied by the above-mentioned Trützschler GmbH and Co. KG known as the TRÜTZSCHLER-TEXNET.

The invention has been illustrated by reference to the example of a carding machine. It can be used in the same way on other spinning preparation machines having a machinery housing, for example openers, cleaners, fiber flock chutes, draw frames, cards and the like.

What is claimed is:

1. A spinning preparation machine comprising:
   a housing having a housing interior;
   two or more working elements housed at least partly within said housing interior;
   a plurality of image-recording systems which are each arranged to generate an image of a surface of one or more of the working elements or of textile fiber material within said housing interior located proximate one or more of the working elements, each resulting image being of a different operational stage in a spinning preparation process and of a surface of a different working element or of textile fiber material located proximate a different working element; and
   at least one display device associated with the plurality of image-recording systems and located exterior to the housing, the at least one display device adapted to display images of surfaces of two or more different working elements or of textile fiber material located proximate two or more different working elements.

2. A spinning preparation machine according to claim 1, in which there is arranged within said housing interior a fiber feed device, one of said image-recording systems being arranged to generate an image of a surface of said feed device or of a textile fiber material travelling through said feed device.

3. A spinning preparation machine according to claim 1, in which there is arranged within said housing interior a fiber discharge device, one of said image-recording systems being arranged to generate an image of a surface of said discharge device or of a textile fiber material travelling through said discharge device.

4. A spinning preparation machine according to claim 1, in which the image-recording systems comprise at least one camera located within said housing.

5. A spinning preparation machine according to claim 1, in which the housing is substantially closed.

6. A spinning preparation machine according to claim 1, the machine being a carding machine wherein said plurality of image recording systems comprises one or more electronic cameras for generating respective images of one or more working elements of said carding machine and/or of fiber material being transported by or between said working elements, wherein said one or more working elements are selected from fiber feed arrangements, licker-ins, carding cylinders, doffers, stripper rollers and card top bars.

7. A spinning preparation machine according to claim 6, in which each camera is arranged to be stationary during operation of the machine.

8. A spinning preparation machine according to claim 1, in which at least one of the image-recording systems comprises at least one camera for generating an image of a waste-extraction device.

9. A spinning preparation machine according to claim 8, in which the waste-extraction device has a window for permitting inspection by said camera.

10. A spinning preparation machine according to claim 1, comprising at least one electronic evaluation device for evaluating the images, and a plurality of electronic cameras connected to said electronic evaluation device.

11. A spinning preparation machine according to claim 10, in which each evaluation device is connected to a control arrangement of the machine and the machine can be controlled in accordance with the evaluated images.

12. A spinning preparation machine according to claim 1, which further comprises a lighting device.

13. A spinning preparation machine according to claim 1, comprising at least two light sources.

14. A spinning preparation machine according to claim 1, comprising at least two light sources of different wavelengths.

15. A spinning preparation machine according to claim 1, in which the image-recording system includes an incident light source for lighting a said surface, and a camera arranged to detect reflect light from said surface.

16. A spinning preparation machine according to claim 1, in which at least one of the image-recording systems is connected to an electronic control and regulation device for the machine, the electronic control and regulating device having a memory for recorded images.

17. A spinning preparation machine according to claim 1, in which at least one of the image-recording systems is arranged to generate an image of one or more regions of the fiber material selected from fiber flocks, fiber flock webs, card webs, fiber sliver, and fiber waste.

18. A spinning preparation machine according to claim 1, in which at least one of the image-recording systems comprise at least one row of electronic cameras for examining fiber material over the working width of the machine.

19. A spinning preparation machine according to claim 1, in which the machine is opener or cleaner.

20. A spinning preparation machine according to claim 1, in which the machine is a carding machine.

21. A spinning preparation machine according to claim 1, in which the image-recording systems comprise a multiplicity of electronic cameras, arranged in staggered relationship relative to one another in the direction of the movement of the fiber material.

22. A spinning preparation machine according to claim 1, in which at least one of the image-recording systems comprises at least one camera that is movable over the width of the machine.

23. A spinning preparation machine according to claim 1, in which the image-recording systems comprise at least one camera that has a CCD sensor.

24. A spinning preparation machine according to claim 1, in which the image recording systems comprise at least one video camera.

25. A carding machine having a housing with a housing interior, two or more working elements of said carding machine substantially enclosed by said housing within said housing interior, and a control device for controlling one or more of said working elements, wherein the machine further comprises a plurality of imaging devices that each monitor a different operational stage in a carding process within said housing interior, each imaging device arranged for transmitting to said control device data recorded from a surface of a different working element or of moving fiber within the housing proximate a different working element, the control device being arranged to process and evaluate the data and adjust one or more working elements of the machine in dependence thereon; and at least one display device associated with the plurality of imaging devices and located exterior to the housing, the at least one display device adapted to display images transmitted by said imaging devices of surfaces of two or more different working elements or of moving fiber located proximate two or more different working elements.

\* \* \* \* \*